United States Patent [19]

Jones et al.

[11] Patent Number: 5,638,454

[45] Date of Patent: Jun. 10, 1997

US005638454A

[54] NOISE REDUCTION SYSTEM

[75] Inventors: Owen Jones; Michael C. J. Trinder, both of Colchester, Great Britain

[73] Assignee: Noise Cancellation Technologies, Inc., Linthicum, Md.

[21] Appl. No.: 190,031

[22] PCT Filed: Jul. 28, 1992

[86] PCT No.: PCT/GB92/01399

§ 371 Date: May 26, 1994

§ 102(e) Date: May 26, 1994

[87] PCT Pub. No.: WO93/03479

PCT Pub. Date: Feb. 18, 1993

[30] Foreign Application Priority Data

Jul. 30, 1991 [GB] United Kingdom .................... 9116433

[51] Int. Cl.[6] ........................ A61F 11/06

[52] U.S. Cl. ........................ 381/71; 381/94

[58] Field of Search ........................ 381/73.1, 71, 94, 381/42, 47, 92; 455/45, 317, 114

[56] References Cited

U.S. PATENT DOCUMENTS

| | | | |
|---|---|---|---|
| 4,334,730 | 6/1982 | Wray | 381/94 |
| 4,506,380 | 3/1985 | Matsui | 381/71 |
| 4,689,821 | 8/1987 | Salikuddin et al. | 381/71 |
| 5,091,947 | 2/1992 | Ariyoshi et al. | 381/42 |
| 5,093,930 | 3/1992 | Kasperkovitz | 455/45 |
| 5,170,433 | 12/1992 | Elliott et al. | 381/71 |
| 5,224,170 | 6/1993 | Waite, Jr. | 381/92 |
| 5,293,578 | 3/1994 | Nagami et al. | 381/71 |

*Primary Examiner*—Curtis Kuntz
*Assistant Examiner*—Vivian W. Chang
*Attorney, Agent, or Firm*—Crowell & Moring

[57] ABSTRACT

A system for reducing periodic noise, which includes a plurality of harmonically related noise signals, comprises an actuator for producing a canceling acoustic signal, a sensor for detecting a residual noise signal, a synchronizing signal generator and processing circuitry. The processing circuitry comprises a plurality of tunable harmonically related band pass filters, a tuning signal generator and a summer which sums the outputs of the filters. The tuning signal generator receives the synchronizing signal from the synchronizing signal generator and outputs the tuning signals to the band pass filters. As the frequency of the synchronizing signal changes, the tuning signal generator causes the tunable filters to track harmonics of the noise to be canceled. After summing by the summer and suitable amplification, the outputs from the filters are used to drive the actuator so as to reduce the residual noise detected by the sensor.

21 Claims, 5 Drawing Sheets

NOISE REDUCTION SYSTEM

FIELD OF THE INVENTION

The present invention relates to noise reduction systems.

BACKGROUND TO THE INVENTION

In the past unwanted noise and vibration has been controlled by muffling or isolation. However, the principle of superposition means that noise and vibration can also be controlled by means of so-called "anti-noise", that is the production of an acoustic signal having the same spectral characteristics as the unwanted noise or vibration but 180° out of phase.

U.S. Pat. No. 4,527,282 discloses a system where a speaker generates a cancelling acoustic signal which is mixed with an unwanted acoustic signal. A microphone senses the residual acoustic signal which is then amplified and inverted to drive the speaker. Systems of this type are prone to instabilities and are restricted in the range of frequencies over which they are effective.

A system which avoids the instability problems of simple systems, such as that disclosed in U.S. Pat. No. 4,527,282, is described in U.S. Pat. No. 4,490,841. In the described system, the residual signal is analysed by means of a fourier transformer. The resultant fourier coefficients are then processed to produce a set of fourier coefficients which are then used to generate a cancelling signal.

Systems which process signals in the frequency domain, following fourier transformation, perform their function well under steady-state conditions. However, if the fundamental frequency of the noise signal changes, the system requires several cycles to re-establish effective cancellation. This is due to the time taken to perform the fourier transformation. If such apparatus is used in an internal combustion engine noise control system, bursts of noise will occur during acceleration and deceleration. These bursts may, in fact, have a higher peak value than the unsuppressed steady-state engine noise. Furthermore, the need to carry out high-speed digital signal processing means that these systems are expensive to implement.

SUMMARY OF THE INVENTION

It is an aim of the present invention to overcome the above disadvantages associated with prior art noise control systems, which process signals in the frequency domain, whilst avoiding the stability problems that have bedevilled simple feedback systems. Surprisingly, it is not recourse to ever more sophisticated, and expensive, digital signal processing which provides a key to overcoming the aforementioned disadvantages in accordance with the invention.

The present invention provides an apparatus for the cancellation of noise or vibrations, comprising: means for producing an electrical error signal representative of the sum of the instantaneous amplitudes of an unwanted periodic acoustic signal and a cancelling acoustic signal; filtering means for filtering the electrical error signal to produce an electrical cancelling signal comprising the filtered electrical error signal; means responsive to the electrical cancelling signal to produce the cancelling acoustic signal for cancelling the unwanted periodic acoustic signal; and control signal generating means for generating a control signal, harmonically related to the unwanted periodic acoustic signal; wherein the filtering means includes a tunable bandpass filter means for filtering the electrical error signal, the filter means being tuned, in response to the control signal, so as to maintain within its passband a frequency harmonically related to the unwanted periodic acoustic signal. Additionally, the gain at resonance of the filter means maybe reduced as a function of the fundamental frequency of the unwanted periodic acoustic signal.

Advantageously, a plurality of narrowband bandpass filters may by provided, tuned to harmonically related frequencies. Preferably, these filters due implemented using switched-capacitor filter techniques.

However, other conventional techniques such as LC filters, using inductors or gyrators, comb filters, transposing filters or digital filters may usefully be employed. If a very high Q switched-capacitor filter is used, a servo loop may be required to suppress any dc offset occuring.

Preferably, an anti-aliasing filter and a compensating filter will be used either around the filtering means or around each filter, if the invention is embodied using digital or switched-capacitor filters.

Under certain circumstances, it may be preferable to implement the narrowband bandpass filter means using an integrator in series with a second order high-pass filter. In this case, the gain of the high-pass filter may be varied as the inverse of the fundamental frequency of the unwanted periodic acoustic signal.

Preferably, a broadband bandpass filter may be connected in parallel with the bandpass filter means in order to provide some reduction in random acoustic signals. The upper −3 dB frequency of the broadband filter may, advantageously, be varied as the inverse of the fundamental frequency of the unwanted periodic acoustic signal.

DETAILED DESCRIPTION OF THE INVENTION

Embodiments of the invention will now be described, by way of example, with reference to the accompanying drawings.

Figure 1:
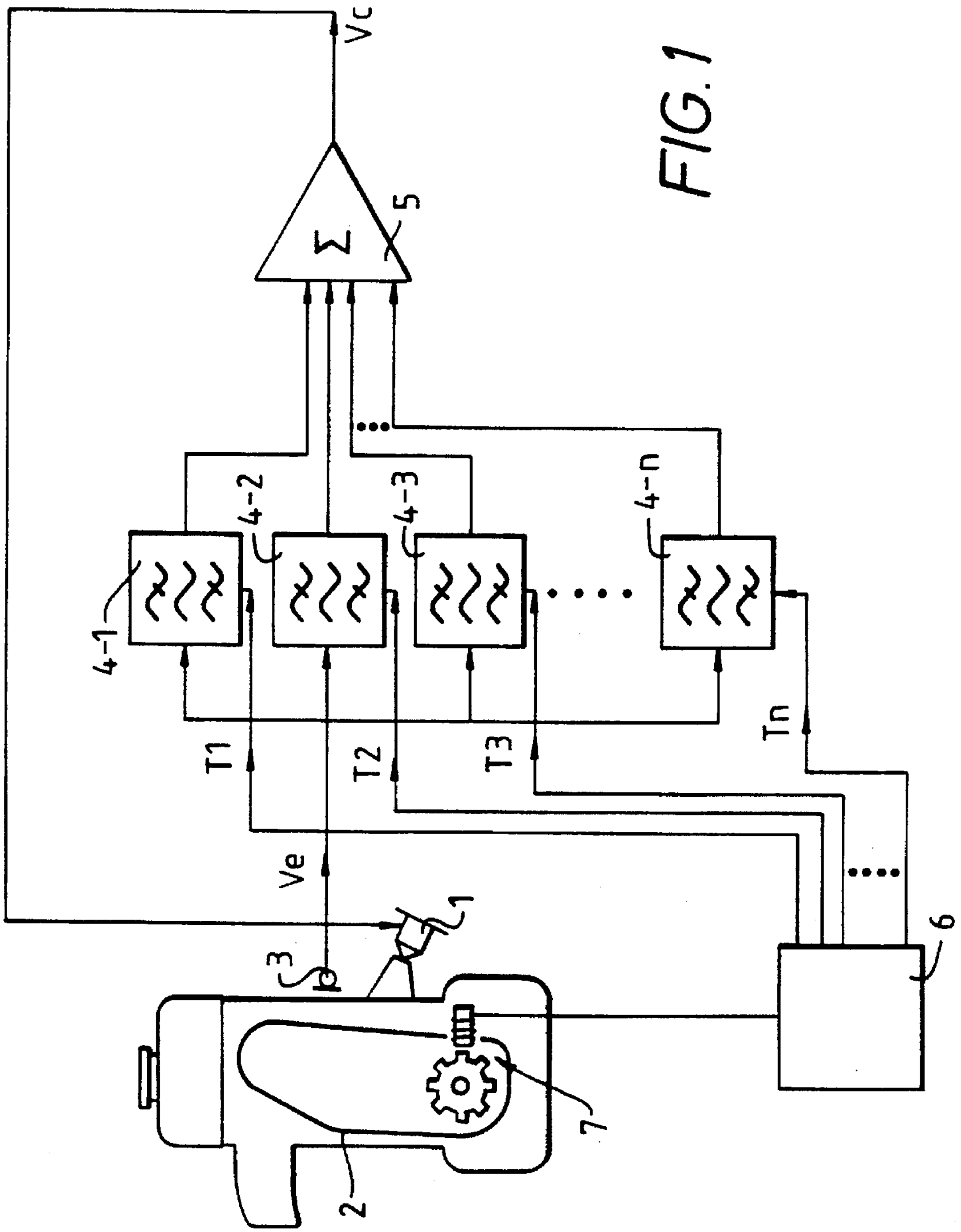
FIG. 1 is a block diagram of an engine vibration control system embodying a basic form of the present invention.

Referring to FIG. 1, an electromagnetic actuator 1 forms a mount for an internal combustion engine 2 in a road vehicle. An accelerometer 3 is positioned on the vehicle body near the actuator 1 to sense the vibrations produced by the engine 2. A bank of switched-capacitor narrowband bandpass filters 4-1 to 4-n are connected to receive the output from the accelerometer 3. The filters 4-1 to 4-n are tuned to a series of harmonically related frequencies e.g. if filter 4-1 is tuned to F, then filter 4-2 is tuned to 2F and so on up to filter 4-n which is tuned to nF. The outputs from the filters 4-1 to 4-n are coupled to respective inputs of a summing amplifier 5. The actuator 1 is coupled to be driven by the output from the summing amplifier 5. A controller 6 receives a train of pulses from a toothed-wheel rotation sensor 7. The rotation sensor is of the type commonly used in electronic engine management systems.

Operation of the internal combustion engine 1 produces vibrations comprising a number of components, related harmonically to the ignition frequency. For instance, a four cylinder four stroke engine running at 3000 rpm will produce a spark for each half cycle i.e. 6000 per minute. This equates to an ignition frequency of 100 Hz. The pulse-like nature of the noise means that it is rich in harmonics, that is 200 Hz, 300 Hz, etc. components. The engine will also produce some broadband vibrations but these are at a much lower level.

Considering the system shown in FIG. 1 with the actuator 1 disconnected from the summing amplifier 5, vibrations generated by the engine 1 is sensed by the accelerometer 3 which outputs an electrical signal Ve, representing the sensed vibrations. The signal Ve is then fed to the filters 4-1 to 4-n.

The filters 4-1 to 4-n are electrically tuned by means of signals T1 to Tn, produced by the controller 6, so that each filter 4-1 to 4-n is tuned to a different frequency component of the vibrations. The controller 6 receives a pulse signal from the rotation sensor 7 which is harmonically related to the speed of the engine crankshaft and, hence, also to the ignition frequency. The signals T1 to Tn are produced by the controller 6 in dependence on the rate of the pulse signal from the rotation sensor 7 and in this way the filters 4-1 to 4-n are caused to track changes in the ignition frequency.

Figure 2A:
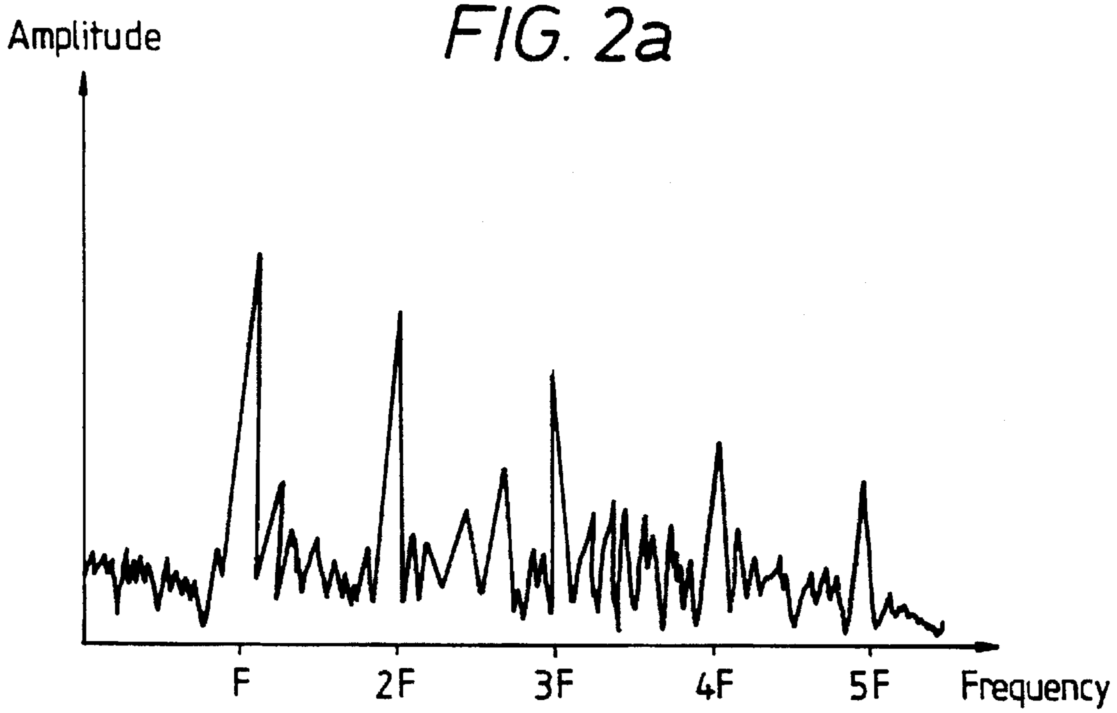
FIG. 2*a* is an idealised representation of the vibration signal from an internal combustion engine.
Figure 2B:
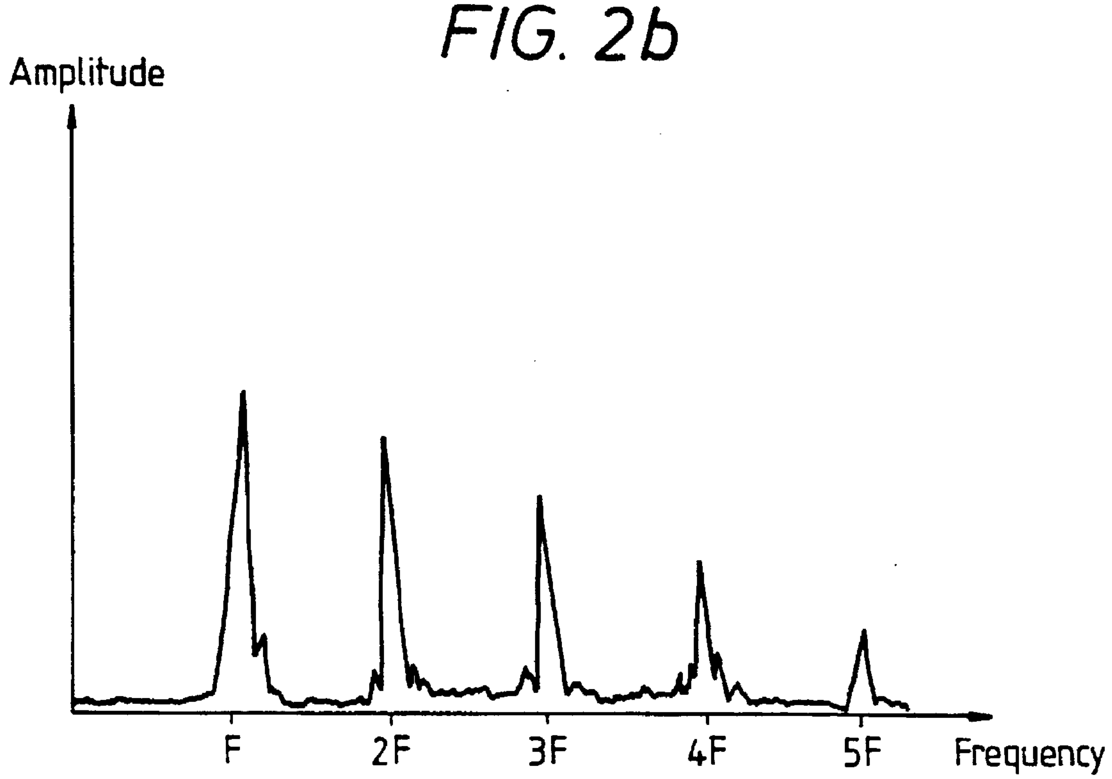
FIG. 2*b* is an idealised representation of the vibration signal after filtering in the absence of a cancelling signal.

It can be seen from a comparison of FIGS. 2*a* and 2*b* that those parts of the vibration spectrum having the highest amplitudes, i.e. the harmonics of the ignition frequency F, are passed substantially unchanged while the remaining, low-level elements are greatly attenuated. Using this technique of parallel harmonically related filters, it is possible to extend the effective bandwidth of the system without encountering stability problems. The use of bandpass filters means that the maximum phase shift occuring in the filter bank is ±90°, making it easier to ensure that the Nyquist Stability Criterion is met by the system.

The outputs from the filters 4-1 to 4-n are fed to a summing amplifier 5 which outputs an actuator control signal Vc. The signal Vc may undergo equalisation or further amplification (not shown) depending on the requirements of the actuator 1 employed.

The system shown in FIG. 1 will now be considered with the actuator 1 reconnected. For correct operation the loop must be designed such that the acoustic signals from the actuator 1 reaching the accelerometer 3 are 180° out of phase with the relevant engine vibration. The signal Ve output from the accelerometer 3 will now be representative of the instantaneous difference between the engine vibration and the acoustic signals from the actuator 1, that is the error between the desired, i.e. no vibration, condition and the total vibration produced by the system.

Figure 3:
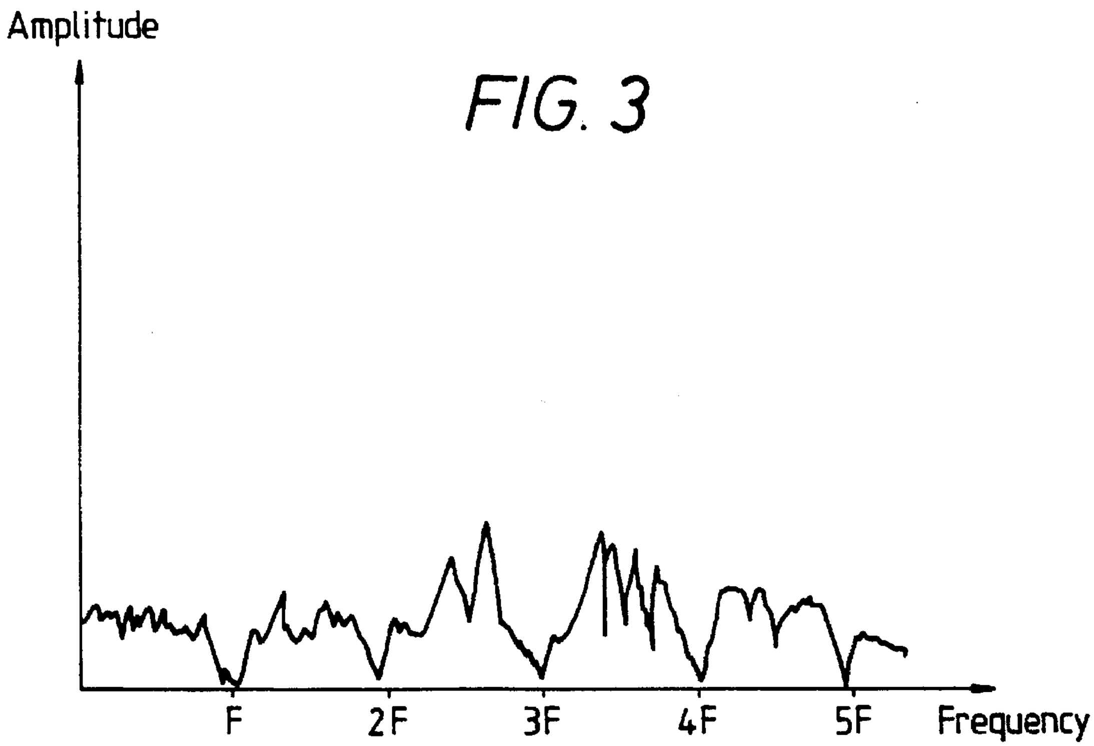
FIG. 3 is an idealised representation of the vibration signal combined with a cancelling signal.

The signal Ve is then filtered and fed to the summing amplifier 5 to produce the signal Vc as in the open loop situation described above. However, since the loop is now closed the vibration components related to the engine ignition will be attenuated. The other vibration components will remain substantially unchanged as no relevant "anti-noise" is being produced because most of the components of the signal Vc, representing these vibration components, are blocked by the filters 4-1 to 4-n. The resulting total vibration occuring in the vehicle body when the system is in operation is shown in FIG. 3.

Since the system does not need to carry out a fourier analysis of the engine noise, it can more closely track changes in engine speed, thereby reducing the bursts of noise during acceleration and deceleration.

As the filters 4-1 to 4-n are of the switched-capacitor type, they may be tuned by varying the switching rate. The switching rate in the embodiment shown in FIG. 1 is controlled by the signals T1 to Tn which are pulse trains frequency locked to harmonics of the ignition frequency.

Figure 4:
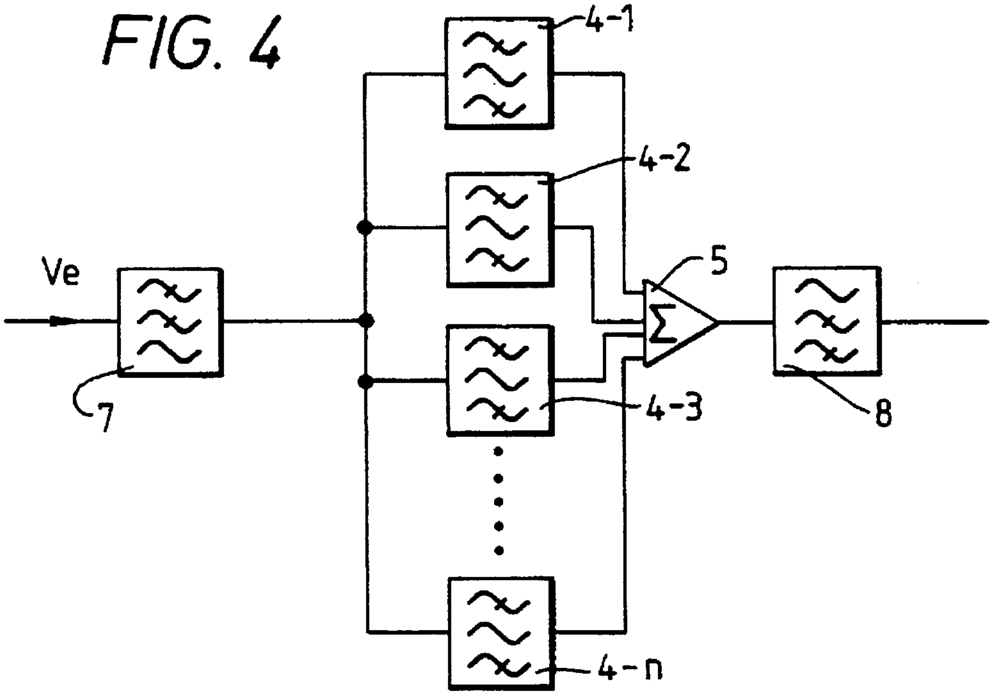
FIG. 4 shows a first arrangement of anti-aliasing and compensation filters.
Figure 5:
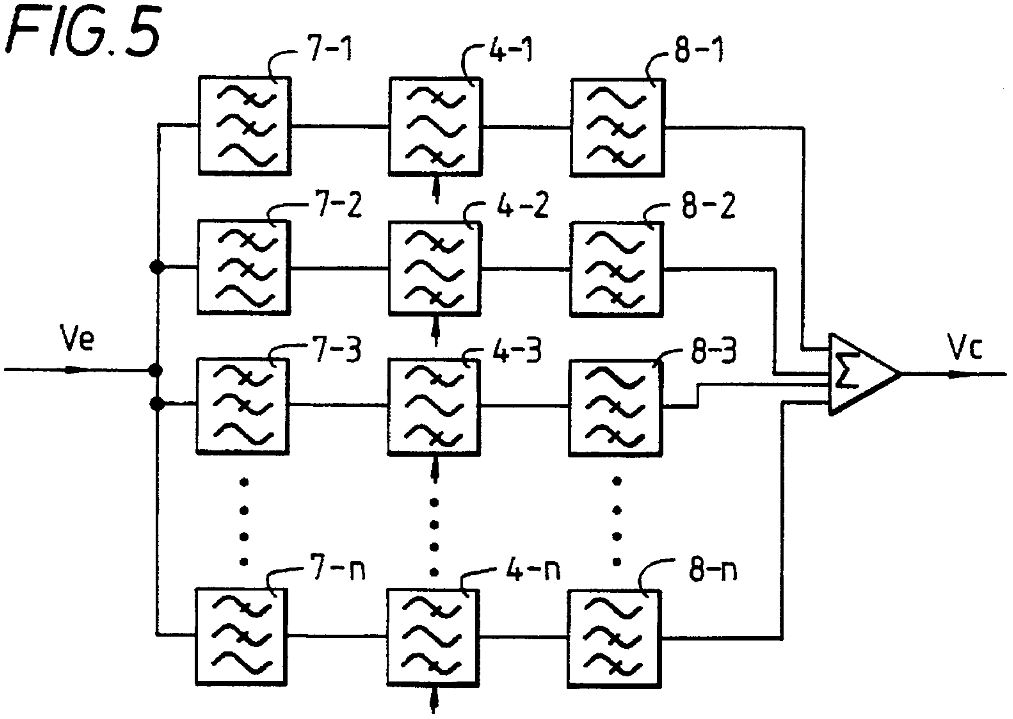
FIG. 5 shows a second arrangement of anti-aliasing and compention filters.

When using filters which have a sampling function such as the switched-capacitor filters 4-1 to 4-n, it is advisable to employ an anti-aliasing filter. However, the inclusion of an anti-aliasing filter introduces unwanted additional phase shifts into the loop. Therefore, a compensating filter should be used after the filters 4-1 to 4-n restore the original phase relationships. Two possible arrangements of anti-aliasing and compensating filters are shown in FIGS. 4 and 5. Referring to FIG. 4, an anti-aliasing filter 7 is inserted before the signal line divides to go to each of the switched-capacitor filters 4-1 to 4-n. A single compensating filter 8 is then inserted after the summing amplifier 5. In the arrangement shown in FIG. 5, an anti-aliasing filter 7-1 to 7-n and a compensating filter 8-1 to 8-n are provided around each switched capacitor filter 4-1 to 4-n.

Figure 6:
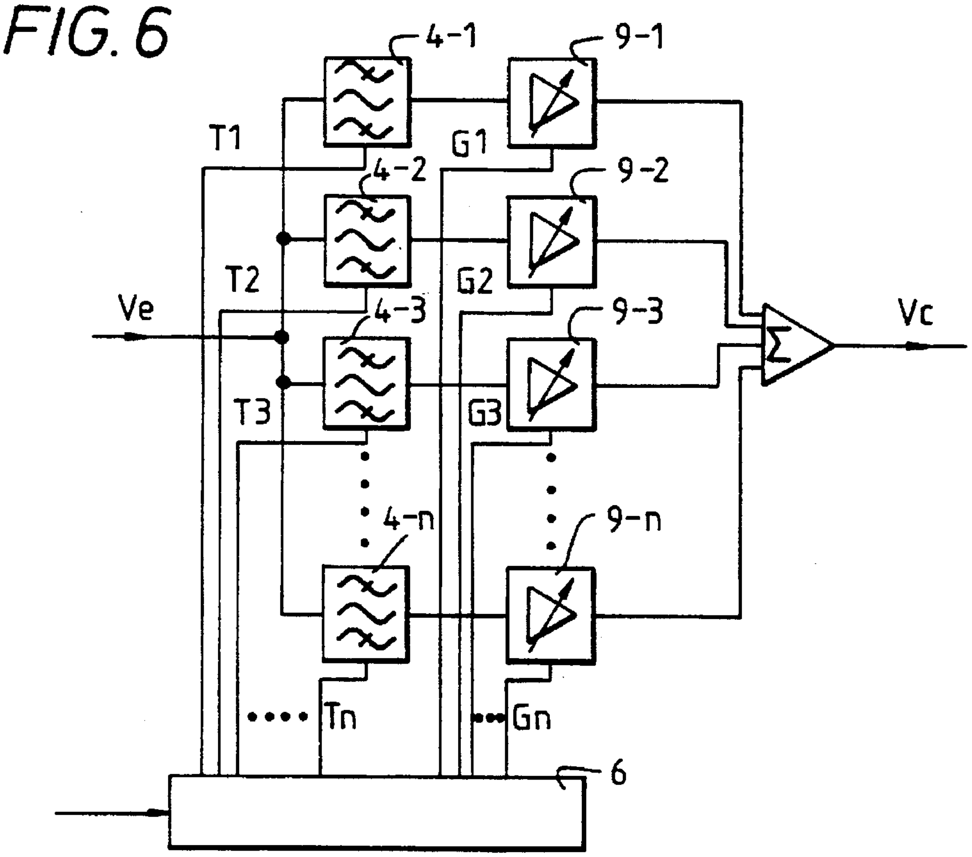
FIG. 6 shows an arrangement for varying the gain of the narrowband bandpass filter means.

In order to ensure the stability of the system as the ignition frequency increases, it may be desirable to reduce the gain of the bandpass filter means. An arrangement which acheives this is shown in FIG. 6. A voltage controlled amplifier 9-1 to 9-n is placed in series, following each of the switched-capacitor filters 4-1 to 4-n. Each amplifier 9-1 to 9-n is controlled by a respective signal G1 to Gn generated by the controller 6. The controller 6 in this case further includes a frequency-to-voltage converter which is arranged to output a dc signal proportional to the ignition frequency. This dc signal is then used to generate the amplifier control signals G1 to Gn.

Figure 7:
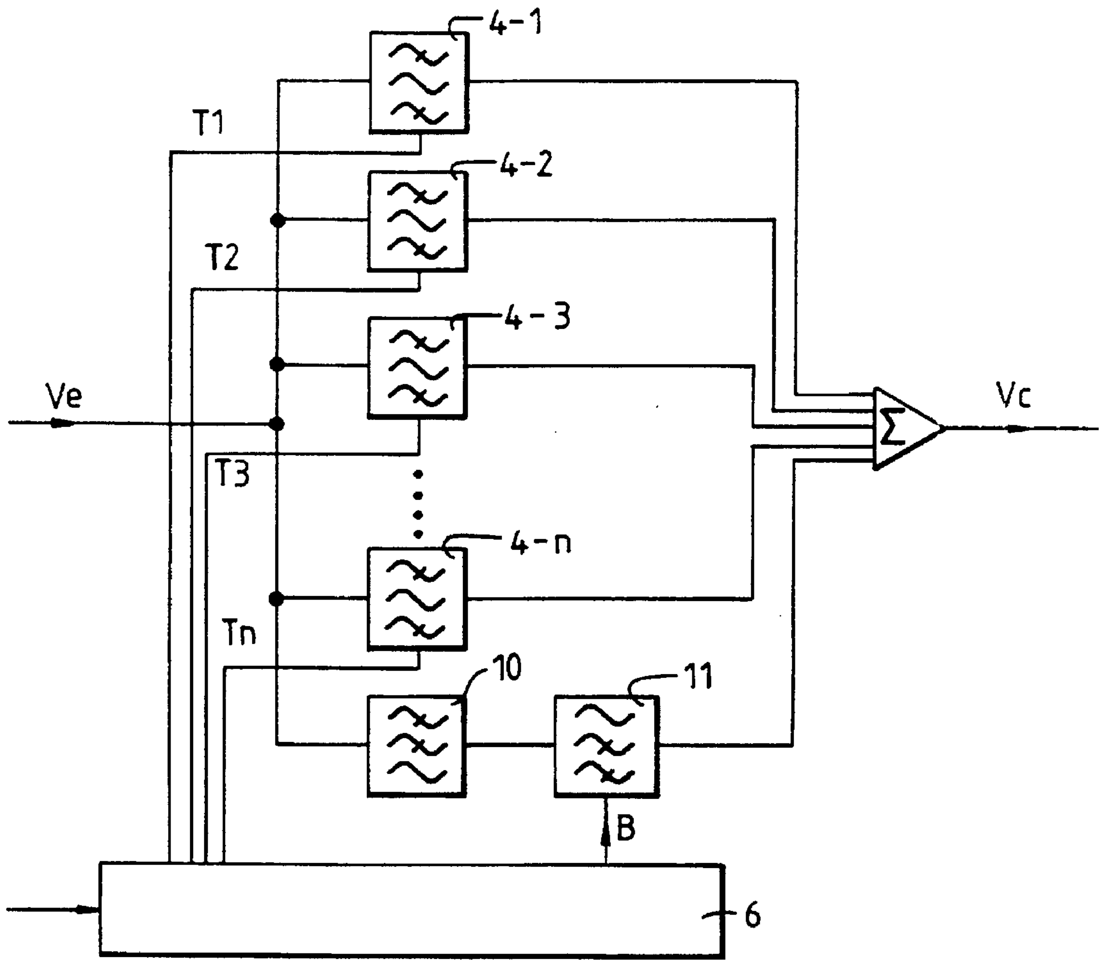
FIG. 7 shows a filter arrangement including a broadband filter.

While the system described above is effective at dealing with periodic acoustic signals, it provides only limited cancellation of random acoustic signals. The random acoustic signal performance of the system may be improved by using a broadband bandpass filter in parallel with the switched-capacitor filters 4-1 to 4-n. In the arrangement shown in FIG. 7, the broadband bandpass filter comprises a high-pass filter 10 followed by a low-pass filter 11. Both filters 10 and 11 are of the switched-capacitor type. The −3 dB frequency of the high-pass filter 10 is fixed. However, the −3 dB frequency of the low-pass filter 11 is variable under the control of the controller 6. The controller 6 outputs a signal B which gradually reduces the −3 dB frequency of the low-pass filter 11 when the ignition frequency rises past a predetermined threshold. This reduction of the low-pass filter −3 dB frequency improves the high frequency stability of the system. If necessary, the −3 dB frequency of the high-pass filter may also be varied as a function of ignition frequency by a similar technique.

The switched-capacitor filters 4-1 to 4-n are constructed using MF10 integrated circuits. Using these circuits it is possible to form filters having extremely high Q values. However, high Q filters of this type are prone to the build-up of dc offset voltages. These may be suppressed by means of a dc servo loop around either each of the filters 4-1 to 4-n or by an averaging dc servo loop around the bank of filters 4-1 to 4-n.

Such a scheme is illustrated in FIG. 4*b*. The integrator compares the bandpass filter output voltage to a reference generating an error signal that is applied to the input of the bandpass filter via the summing junction to correct any error in output voltage. The phase of the feedback signal is arranged to ensure that the overall loop is inverting. The circuit can be simplified as in FIG. 4*c* by applying the servo loop around the whole filter bank instead of individually around each individual bandpass filter, but in this case the loop will only correct the average of the filter outputs.

Figure 8:
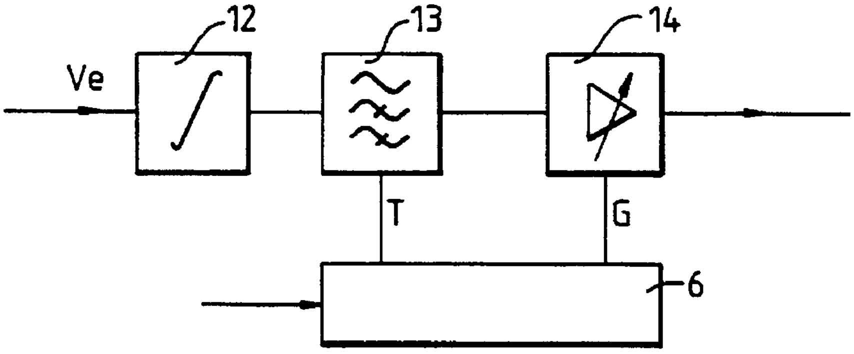
FIG. 8 shows alternative narrowband bandpass filter means.

An alternative to a switched-capacitor bandpass filter is the series combination of an integrator 12 and a second order high-pass filter 13, see FIG. 8. In the system shown in FIG. 1, each of the switched-capacitor filters 4-1 to 4-n would be replaced by the combination an integrator 12 and a high-pass filter 13. The high-pass filter 13 may be implemented using a switched-capacitor techniques, in which case its −3 dB frequency would be varied under the control of the controller 6 in order to tune the combination. However, as the ignition frequency increases the gain of the bandpass filter as a whole will fall. This can be compensated for by means of a voltage controlled amplifier 14 which is also under the control of the controller 6. The controller 6 outputs to the amplifier 14 a signal G, dependent on the ignition frequency, which causes the gain of the amplifier 14 to increase as the ignition frequency increases.

While the present invention has been described with reference to an engine vibration control system, it is not limited thereto and is applicable to many situations where it is desirable to cancel an acoustic signal. Acoustic signal includes longitudinal sound waves in solids, liquids or gases, vibrations and flexure.

In the embodiments described above, the system is used to isolate engine vibrations from a vehicle body. If, however, the accelerometer were affixed to the engine, the system would operate to cancel the vibrations in the engine itself. Therefore, it will be appreciated that the present invention can be employed for beth isolating and directly cancelling unwanted periodic acoustic signals.

Furthermore, the present invention will find application in many different situations, for instance to quieten a refrigerator, in an active exhaust muffler or to cancel fan noise in ducting.

We claim:

1. An apparatus for cancelling of noise or vibrations, comprising:

means for producing an electrical error signal representative of the sum of the instantaneous amplitudes of an unwanted periodic acoustic signal and a cancelling acoustic signal;

filtering means for filtering the electrical error signal to produce an electrical cancelling signal comprising the filtered electrical error signal;

means responsive to the electrical cancelling signal to produce the cancelling acoustic signal for cancelling the unwanted periodic acoustic signal; and control signal generating means for generating a control signal, harmonically related to the unwanted periodic acoustic signal;

wherein the filtering means includes a tunable bandpass filter means for filtering the electrical error signal, the filter means being tuned, in response to the control signal, so as to maintain within its passband a frequency harmonically related to the unwanted periodic acoustic signal.

2. An apparatus according to claim 1, wherein the processing means includes a plurality of harmonically related bandpass filter means arranged in parallel and adaptable, in reponse to the control signal, to maintain within their respective passbands respective frequencies harmonically related to the unwanted periodic acoustic signal.

3. An apparatus according to claim 2, wherein an anti-aliasing filter and a compensating filter are provided for each bandpass filter means.

4. An apparatus according to claim 2, wherein the bandpass filter means comprises a switched capacitor filter.

5. An apparatus according to claim 4, wherein the bandpass filter means is provided with a servo loop arranged to suppress the occurrence of a dc offset voltage.

6. An apparatus according to claim 2, wherein the processing means further comprises anti-aliasing filter means located before the bandpass filter means and compensation filter means located after the bandpass filter means.

7. An apparatus according to claim 2, wherein the gain of the bandpass filter means at resonance decreases as the fundamental frequency of the unwanted periodic acoustic signal increases.

8. An apparatus according to claim 2, further comprising further bandpass filter means, having a passband substantially greater than that of said first bandpass filter means, arranged in parallel with the first bandpass filter means.

9. An apparatus according to claim 1, wherein the bandpass filter means comprises a switched capacitor filter.

10. An apparatus according to claim 9, wherein the bandpass filter means is provided with a servo loop arranged to suppress the occurrence of a dc offset voltage.

11. An apparatus according to claim 1, wherein the processing means further comprises anti-aliasing filter means located before the bandpass filter means and compensation filter means located after the bandpass filter means.

12. An apparatus according to claim 11, wherein the gain of the bandpass filter means at resonance decreases as the fundamental frequency of the unwanted periodic acoustic signal increases.

13. An apparatus according to claim 11, further comprising further bandpass filter means, having a passband substantially greater than that of said first bandpass filter means, arranged in parallel with the first bandpass filter means.

14. An apparatus according to claim 1, wherein the bandpass filter means comprises an integrator connected in series with a second order high pass filter whose output is connected to a gain controlled amplifier.

15. An apparatus according to claim 14, wherein the gain of the bandpass filter means is increased as the fundamental frequency of the unwanted periodic acoustic signal increases.

16. An apparatus according to claim 1, wherein the gain of the bandpass filter means at resonance decreases as the fundamental frequency of the unwanted periodic acoustic signal increases.

17. An apparatus according to claim 1, further comprising further bandpass filter means, having a passband substantially greater than that of said first bandpass filter means, arranged in parallel with the first bandpass filter means.

18. An apparatus according to claim 17, wherein the upper −3 dB frequency of the further bandpass filter means is reduced as the fundamental frequency of the unwanted periodic acoustic signal increases.

19. An apparatus according to claim 18, wherein the lower −3 dB frequency of the second bandpass filter means is varied as a function of the fundamental frequency of unwanted periodic acoustic signal.

20. An apparatus according to claim 17, wherein the lower −3 dB frequency of the second bandpass filter means is varied as a function of the fundamental frequency of unwanted periodic acoustic signal.

21. An apparatus according to claim 14, wherein the gain controlled amplifier is a voltage controlled amplifier.

* * * * *